US009632047B2

(12) United States Patent
Gruden et al.

(10) Patent No.: US 9,632,047 B2
(45) Date of Patent: Apr. 25, 2017

(54) METHOD AND DEVICE FOR THE DETECTION OF PROPERTIES OF FLUID MEDIA

(71) Applicant: Seuffer GmbH & Co. KG, Calw (DE)

(72) Inventors: Roman Gruden, Pforzheim (DE); Volker Beck, Wurmberg (DE)

(73) Assignee: SEUFFER GMBH & CO. KG, Calw (DE)

( * ) Notice: Subject to any disclaimer, the term of this patent is extended or adjusted under 35 U.S.C. 154(b) by 765 days.

(21) Appl. No.: 14/031,233

(22) Filed: Sep. 19, 2013

(65) Prior Publication Data
US 2014/0077828 A1    Mar. 20, 2014

(30) Foreign Application Priority Data

Sep. 19, 2012 (DE) .................. 10 2012 018 539

(51) Int. Cl.
*G01N 27/02* (2006.01)
*D06F 39/00* (2006.01)
(Continued)

(52) U.S. Cl.
CPC ........ *G01N 27/026* (2013.01); *A47L 15/4297* (2013.01); *D06F 39/004* (2013.01); *G01N 33/182* (2013.01)

(58) Field of Classification Search
CPC .. G01N 27/026; G01N 33/182; G01N 21/251; D06F 39/004; A47L 15/4297; A47L 2501/26; Y10T 74/2109
See application file for complete search history.

(56) References Cited

U.S. PATENT DOCUMENTS

| 5,731,868 A * | 3/1998 | Okey .................. A47L 15/4297 356/442 |
| 2005/0017728 A1* | 1/2005 | Kaiser .................. G01N 27/221 324/453 |

(Continued)

FOREIGN PATENT DOCUMENTS

| DE | 217557 C | 1/1910 |
| DE | 4311064 A1 | 10/1994 |

(Continued)

OTHER PUBLICATIONS

Robert et al. DE202011101482 (English Translation), pub date Sep. 7, 2012.*

(Continued)

*Primary Examiner* — John Breene
*Assistant Examiner* — Mohammad Islam
(74) *Attorney, Agent, or Firm* — Ware, Fressola, Maguire & Barber LLP

(57) ABSTRACT

A method and apparatus for detecting properties of fluid media within a predefined process using impedance spectroscopy, the method detecting an initial impedance curve, including a plurality of characteristic points on said initial impedance curve determining an initial value of the properties of the fluid medium, determining respective surrounding frequency ranges around each of the characteristic points, conducting further detections of current impedance curves determining respective characteristic points of the current detections within the surrounding frequency ranges of the initial impedance curve, determining differences between the characteristic points of each of the current detections of the impedance curve for at least one of the characteristic points and the respective corresponding characteristic point on the initial impedance curve and comparing the difference with a predetermined reference range, and performing control measures on the process for the purpose (Continued)

of continuing said process if said difference is within the reference range.

16 Claims, 5 Drawing Sheets

(51) Int. Cl.
*A47L 15/42* (2006.01)
*G01N 33/18* (2006.01)

(56) References Cited

U.S. PATENT DOCUMENTS

| | | | | |
|---|---|---|---|---|
| 2005/0173267 | A1* | 8/2005 | Muthuswamy | G01N 29/036 205/792 |
| 2005/0179449 | A1 | 8/2005 | Wooton et al. | |
| 2010/0050345 | A1* | 3/2010 | Kim | D06F 39/004 8/159 |
| 2011/0018728 | A1* | 1/2011 | Uhlhorn | A47L 15/4297 340/657 |
| 2012/0037187 | A1* | 2/2012 | Fuglein | A47L 15/0021 134/18 |

FOREIGN PATENT DOCUMENTS

| | | |
|---|---|---|
| DE | 19610115 A1 | 9/1997 |
| DE | 19755418 A1 | 6/1999 |
| DE | 10018745 A1 | 4/2001 |
| DE | 10228811 A1 | 1/2004 |
| DE | 10351390 A1 | 6/2005 |
| DE | 60307108 T2 | 8/2007 |
| DE | 102008027038 A1 | 12/2009 |
| DE | 20 2011 101482 U1 | 9/2012 |
| DE | 202011101482 U1 * | 9/2012 ........... G01N 27/026 |

OTHER PUBLICATIONS

Roman Gruden, et al; "Influence of surface effects on the characteristic curves of detergent sensors;" 2012 9th International Multi-Conference on Systems, Signals and Devices (SSD 2012); Chemnitz, Germany, Mar. 20-23, 2012, pp. 1-6.

P. Kurzweil, et al; "A new monitoring method for electrochemical aggregates by impedance spectroscopy;" Journal of Power Sources, Elsevier SA, CH, Bd. 127, Nr. 1-2; Mar. 10, 2004; pp. 331-340.

Helinando P. De Oliveira, et al;"Use of Electrical Impedance Spectroscopy as a Practical Method of Investigating the Formation of Aggregates in Aqueous Solutions of Dyes and Surfactants;" The Journal of Physical Chemistry B, Bd. 115, Nr. 21, Jun. 2, 2011; pp. 6903-6908.

* cited by examiner

METHOD AND DEVICE FOR THE DETECTION OF PROPERTIES OF FLUID MEDIA

CROSS REFERENCE TO RELATED APPLICATIONS

This application claims priority under 35 USC §119 to German Patent Application No. 10 2012 018 539.1 filed on Sep. 19, 2012, which application is hereby incorporated by reference in its entirety.

TECHNICAL FIELD

The present invention relates to a method and an apparatus for detecting properties of fluid media, and in particular to a method and an apparatus for detecting properties of aqueous media with impedance spectroscopy.

BACKGROUND OF THE INVENTION

In private households and in industrial applications, there is a general need for information concerning the properties of fluid media. Fluid media may be any fluid consumables such as aqueous media in the form of aqueous solutions of chemical substances, or oils and the like. It is necessary to detect the properties of the respective fluid media in order to determine basic properties when using these media, to identify any changes occurring during operation, and specifically to detect any contamination by foreign matter in a given fluid medium. Depending on the detected measured values and the conclusions reached by analyzing said data, it is possible to decide whether the fluid medium still meets predetermined requirements in its current state, or whether measures for cleaning or for replacing the fluid medium are necessary.

A lucid example of a fluid medium and in particular of an aqueous solution is the detergent solution that is processed in a washing appliance (washing machine, washing device) for cleaning clothes or other objects. Prior art methods and apparatuses involving tests on a detergent solution are described below.

Document DE 217 557 A1 discloses a method and an associated apparatus for controlling the addition of detergents or rinsing agents in washing appliances, with various sensors being arranged in the washing appliance in order to determine the physical and chemical properties of the detergent solution. Any change in the rise of the measurement signal during the addition of detergent or rinsing agents is detected and analyzed by an electronic circuit for analyzing the output signals of the sensors. In combination with the results of analysis, it is possible to control the dosing of detergent for the washing machine.

Document DE 197 55 418 A1 discloses a sensor element and an apparatus for measuring complex impedances in materials, said sensor element having two electrodes which are made of a conductive material and arranged at a predetermined distance from each other. The two electrodes are covered with a thin insulating layer, said insulating layer being relatively thin in comparison with the predetermined spacing between the electrodes. The sensor element thus formed is largely insensitive to the ambient conditions whose properties are to be detected. The output signals from the sensors are subjected to further processing in an evaluation circuit, and the properties of a respective liquid between the electrodes can be analyzed during such processing. More specifically, it is possible for complex impedances to be determined and analyzed as a measure of the liquids' properties.

In the private and industrial spheres, clothes are generally cleaned fully automatically, to a large extent, using electronically controlled washing appliances that are also called fully automatic washing machines. One overall aim of a washing process is to obtain optimal results with minimal consumption of water, electrical energy, thermal energy and detergent. Present-day washing appliances use optical measurement methods for detecting the turbidity of a detergent solution, in order to determine a detergent concentration at least approximately, as well as other methods, but these generally require complex analysis of data. Turbidity sensors often have low levels of accuracy, and the measurement result can be easily distorted by deposits in the vicinity of the turbidity sensor. In washing appliances, such deposits frequently occur in the form of detergent and dirt residues.

Important parameters associated with washing programs are the water hardness, as a basic parameter, the detergent concentration and the washing activity. As regards the current hardness of the water fed into a given washing appliance (generally fresh water or drinking water), municipal water works usually state a value that is at least safe. Based on this information, an amount of detergent can be determined according to the dirtiness of the laundry. It is clear in this regard that only rough estimates can be made here, with which it is barely possible to dimension an optimal amount of detergent with real precision.

Precise determination of the "water hardness" is an important basis for efficient and economical cleaning of textiles, although the expression "water hardness" mainly relates to the concentration of alkaline earth metal ions dissolved in the water. "Total hardness" mainly refers to the calcium and magnesium ions dissolved in the water, and also to their anionic partners such as $HCO_3^-$. From a generalized perspective, detecting the properties of a fluid medium such as water involves all the substances dissolved in the water, as well as any substances that may affect the washing process.

The water hardness, and the dissolved substances it entails, are disadvantageous for washing processes and for processing that involves heating the water.

In municipal water works, the water hardness, in particular the "total hardness", is determined under laboratory conditions by a quantitative analysis in the form of titration. In a sample solution containing a known substance in an unknown concentration, a known substance is added in a known concentration (a "standard solution"), and the volume of standard solution that reacts with the analyte is measured. Based on the consumed volume of standard solution, it is possible to calculate the unknown concentration of a particular substance in the sample solution.

It is clear that quantitative analysis by titration generally requires laboratory conditions that are complicated and costly due to the apparatus and equipment required, and it is also necessary to add a standard solution with a precisely determined concentration to the sample solution. Using quantitative analysis by titration is therefore reserved for a well-equipped laboratory and cannot be applied in this form for simple and quick detection of the properties of a fluid medium such as water, for example, in general industrial applications or in private households.

Since washing processes and the detergents used are increasingly seen in terms of environmental protection aspects, it is necessary to dose not only a particular amount of water but also a particular amount of detergent according to the dirtiness of laundry, and it is also necessary to take into consideration the properties of the water (generally drinking water). Systematic and correct dosing of detergent results in energy and water savings, as well as a lower pollutant load in the wastewater. The properties of the water are another criterion, besides the dirtiness of the laundry, because they have to be taken into consideration when dosing the detergent.

One aim in this connection should be that a device for detecting, for example, the properties of fluid media such as the water or detergent solution supplied to a washing appliance, is simple in design and reliable in operation. Ideally, every washing appliance should be equipped with at least such device so that the required amount of detergent can be determined precisely in the washing appliances. This requires a simple and cost-efficient design, preferably in the form of a module, as well as uncomplicated and therefore cost-efficient assembly, since it can be expected that when such detection devices for washing appliances are used, then large numbers of them will be involved.

SUMMARY OF THE INVENTION

The object of the present invention is therefore to design a method and an apparatus for detecting properties of fluid media such that the properties of fluid media can be measured precisely and continuously in a simple manner and with reduced effort and expense, and that the apparatus can be mass produced at low cost.

According to the invention, this object is achieved by the features of a method and an apparatus as specified in the claims.

The method for detecting properties of fluid media within a predetermined process using impedance spectroscopy comprises the following steps: detecting an initial impedance curve, including a plurality of characteristic points on said initial impedance curve in a complex impedance plane, and determining an initial value of the properties of the fluid medium, determining respective surrounding frequency ranges around each of the characteristic points according to the initial impedance curve, conducting further detections of current impedance curves within the respective surrounding frequency ranges around the characteristic points of the initial impedance curve, determining respective characteristic points of the current detections within the surrounding frequency ranges of the initial impedance curve, determining differences between the characteristic points of each of the current detections of the impedance curve for at least one of the characteristic points and the respective corresponding characteristic point on the initial impedance curve and comparing the difference with a predetermined reference range, and performing control measures on the process for the purpose of continuing said process if said difference is within the reference range.

The apparatus according to the invention comprises at least the devices for performing the respective steps of the method according to a first embodiment.

With the inventive method and apparatus for detecting the properties of the fluid medium, said apparatus having a sensor unit whose signals are formed according to respective actuation in connection with impedance spectroscopy, it is possible for the properties of the fluid medium, and in particular the properties of an aqueous medium such as water (fresh water or drinking water) for filling a washing device, to be determined easily and with relatively high precision. Based on this determination, which involves a comprehensive analysis of the water in respect of the dissolved substances affecting the washing process, the washing process can be efficiently influenced by influencing the operation of the washing device, such as the amount of detergent and water to be added and the number of rinsing operations, in such a way that very good results can be obtained while also conducting the washing process economically and with minimal pollution of the environment.

The sensor unit is actuated in such a way that the plot of a complex impedance Z and the corresponding components of the complex impedances of the medium (a real portion Re(Z) and an imaginary portion (Im(Z)) are determined according to a predetermined frequency range, depending on the frequency. This impedance curve is used as an initial impedance curve which is detected (measured) and stored at the beginning of a procedure or process. The control unit is provided to analyze the detection signal as the output signal from the sensor, at least one characteristic point and preferably a plurality of characteristic points along the curve of complex impedance Z (i.e. the initial impedance curve) being determined in association with said analysis of the detection signal. Depending on a comparison of characteristic points currently measured during the process with the characteristic points obtained from the initial impedance curve (which may represent a reference measurement), it is possible for the properties of the fluid medium to be determined with regard to different aspects. More particularly, differences between corresponding characteristic points are determined as a measure for the properties of the fluid medium.

With the solution according to the invention, it is possible to determine different properties of fluid media, for example a concentration of detergent in a detergent solution, or hardness of fresh water, such that measures can be taken by a consumer, depending on the detected properties, to achieve optimal results, also with regard to low environmental impact. The method and the apparatus according to the present invention for detecting properties of fluid media thus allow accurate and continuous detection in a simple manner, wherein the sensor unit is exposed to the medium and detection is performed by actuating the sensor accordingly via the control unit, and actuation is performed in association with impedance spectroscopy. At least one characteristic point or a plurality of characteristic points may be determined that can be compared with respective basic data in a store.

It is therefore possible to provide desired information quickly to the user of a household appliance, or in an industrial application, or to send the information in a targeted manner to other control or regulator units, so that measures to optimize a process can be carried out. This pertains, for example, to the dosing of detergents in water with a particular hardness. Analysis is specifically limited to the surroundings of the characteristic points, so it is possible in this way to reduce the volume of data significantly and hence to reduce the time needed for analysis. In combination with a simple sensor arrangement, this opens up the possibility of using the apparatus and the method according to the present invention in an automated system, in the case of an industrial application, and also in household appliances, the respective user no longer needing any additional measures or further training to use the respective appliances.

Depending on the particular medium, for example when using impedance spectroscopy to determine the total water hardness or the water value, the characteristic points for said medium are determined, in connection with the previously defined or detected initial impedance curve, and the frequency ranges surrounding these points are defined according to the position of said characteristic points according to the initial impedance curve. The current measurements are taken within the surrounding frequency ranges, and a new position of the respective characteristic point (in the form of frequency values) is determined with said measurements. A resultant signal for the properties of the medium is obtained from the new position of the respective characteristic point, determined for particular frequency information from the current measurement within a respective surrounding frequency range relative to the previous measurement of the initial impedance curve. More particularly, it is possible in the present case and in the application described to determine the water value as a comprehensive property of the water that is significantly better than the total fresh water hardness hitherto known as a special and current property of the water.

Other embodiments of the invention are described in the dependent claims.

The reference range can be determined according to the initial value of the properties of the fluid medium, and the initial value of the properties may lie within the reference range.

The step of determining the difference between the characteristic points may include the step of determining the difference between respective corresponding characteristic points within the respective surrounding frequency range.

The step of conducting further detections may include the step of determining the current impedance curve within the surrounding frequency ranges of the respective characteristic points.

The step of determining the difference between the respective characteristic points may include the step of determining the difference individually for each of the characteristic points or for all the characteristic points that are used.

The reference range of differences between the respective characteristic points may have an upper and a lower limit, and the upper and lower limits can be defined according to respective predetermined differences from the initial value. The upper and the lower limits of the range of differences may be determined according to the kind of process.

The method may also include detecting the properties of the fluid medium by means of voltammetry, and correlating the detection results using voltammetry with the detection results using impedance spectroscopy in order to form a total result in respect of the properties of the fluid medium, thus obtaining a total result that is very precise and comprehensive.

A control unit for determining the characteristic points at predetermined frequencies within the surrounding frequency range may be provided in the apparatus. The apparatus may also include a sensor device for conducting detections in respect of the fluid medium, and the control unit may also be provided to actuate the sensor device to conduct detections using impedance spectroscopy or voltammetry.

In the method and the apparatus according to a second embodiment, the control unit also includes the option of conducting measurements or detections using the cyclic voltammetry method (CV), in addition to the devices and options provided by the first embodiment and therefore in addition to the possibility of conducting any number of detections by means of impedance spectroscopy (detection of impedance curves). The cyclic voltammetry method may be performed independently of impedance spectroscopy, and the control unit is able to have detection carried out by voltammetry using the same sensor unit. Respective detection results can be correlated with each other to obtain a precise overall result for the properties of fluid media.

BRIEF DESCRIPTION OF THE DRAWINGS

The invention shall now be described on the basis of embodiments and with reference to the Figures, in which.

DESCRIPTION OF PREFERRED EMBODIMENTS

The structure and the manner of operation of the inventive method and apparatus according to the invention shall now be described for a first embodiment.

Figure 1:
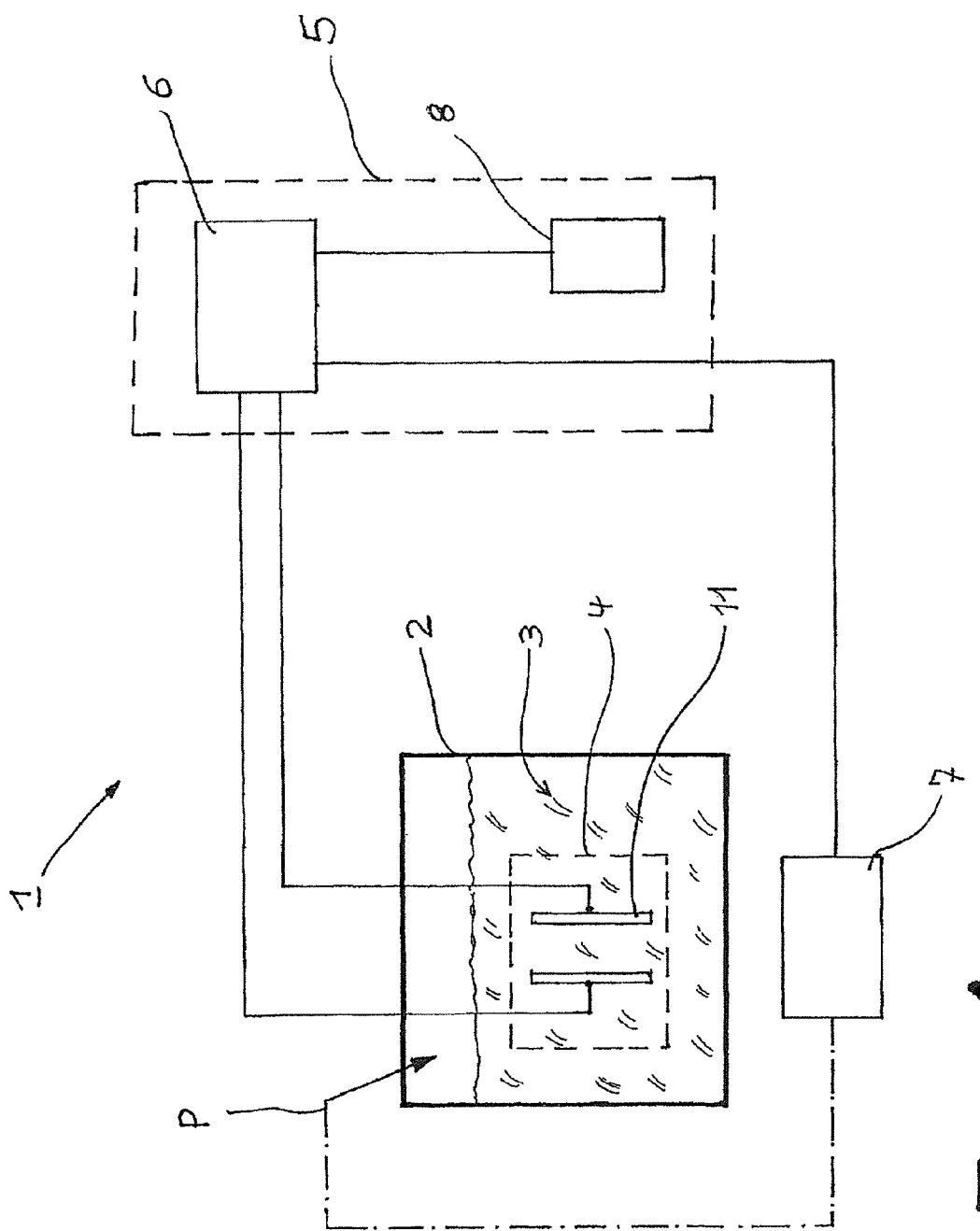
FIG. 1 shows a block diagram of a circuit arrangement (apparatus) for performing impedance spectroscopy.

FIG. 1 shows the apparatus 1 for detecting properties of fluid media (referred to hereinafter in simplified form as "apparatus 1"), said apparatus 1 being disposed in a container 2 in contact with a fluid medium 3 located therein. The expression "container" should be understood in a general sense, and the container may be a tank in a machine, for example, or the drum of a washing device (washing machine), or any container with fresh water. The present invention is not limited to any one of these container types. In any case, container 2 contains the fluid medium whose properties are to be detected, for example fresh water from a municipal water work, in an amount sufficient for the properties of the medium to be detected by means of a sensor device 4. Sensor unit 4 is therefore surrounded wholly or at least partially by medium 3 and must be surrounded by the medium to such an extent that sufficiently reliable measurement is possible. The expression "medium" must likewise be interpreted in a very general sense, since any fluid medium, such as aqueous solutions, detergent solutions, various kinds of oil and the like can be subjected to measurement. To simplify description, the present invention is described below in connection with the testing of water or aqueous solutions, but without being limited thereto.

According to FIG. 1, apparatus 1 also includes a control device 5, which is used to control and/or regulate all the procedures for detection using impedance spectroscopy, and which also causes sensor device 4 to be actuated, and which performs an analysis of the signals (detection signals) outputted by sensor device 4.

For this purpose, control device 5 has an actuation device 6, which is connected to sensor unit 4 and which actuates sensor device 4 with respective electrical signals according to instructions and commands generated inside control device 5. For example, currents and voltages are applied to sensor device 4, in connection with predetermined frequencies or frequency ranges, in order to perform respective measurements. Control device 5 may also be provided to detect the temperature of medium 3 and for that purpose may be connected to a temperature detection device (not shown in the Figures). Alternatively, actuation device 6 may also be disposed as a separate unit outside of control device 5. In this alternative arrangement, sensor unit 4 and actuation device 6 may be functionally combined to form a single measuring device.

Control device 5 is also connected to a control unit 7, which is directly linked to container 2. If it is assumed, for example, that container 2 is the drum of a washing device (washing appliance, washing machine) or is connected to a fresh water inlet of the washing device, then the control unit is the actual device for electronically controlling the washing device. In the washing device, the volume of water, the supply of detergent, the water temperature, the timing of a washing process, as well as spin times and spin speeds are controlled in the respective programmed manner. Depending on the measurement results obtained from sensor device 4, control device 5 may influence control unit 7 such that a larger or smaller amount of water or detergent can be used, in deviation from a predetermined program, or such that a change can be made to the washing temperature, for example. Control device 5, in combination with control unit 7, thus allows variable control of the washing device, or regulation of individual functions of the washing device. In FIG. 1, the influence exerted on the washing process by control unit 7 is indicated schematically by arrow P.

Control device 5 also includes a storage device 8, in which respective data and programs are stored for the detection of material properties using impedance spectroscopy. Said data and programs can be accessed inside control device 5.

With regard to the manner of operation of the device shown in FIG. 1, sensor unit 4 is supplied with predetermined signals in respect of the physical variables such as current, voltage and frequency, in accordance with instructions which are generated inside control device 5 in association with actuation device 6, and the detection signals from sensor unit 4 are received and processed inside control device 5 via actuation device 6, and in combination with programs or data fetched from storage device 8, where relevant. Basic data, or detection data generated in previous measurements, can be stored in storage device 8, so that it is possible, for example, to compare currently measured data with basic data with regard to the properties of the fluid medium 3 being detected. Depending on the result of detection and a result of comparison, control unit 7 may be instructed, in the case of a washing device, to alter or to maintain particular operating parameters (detergent concentration, amount of water, temperature).

Figure 2:
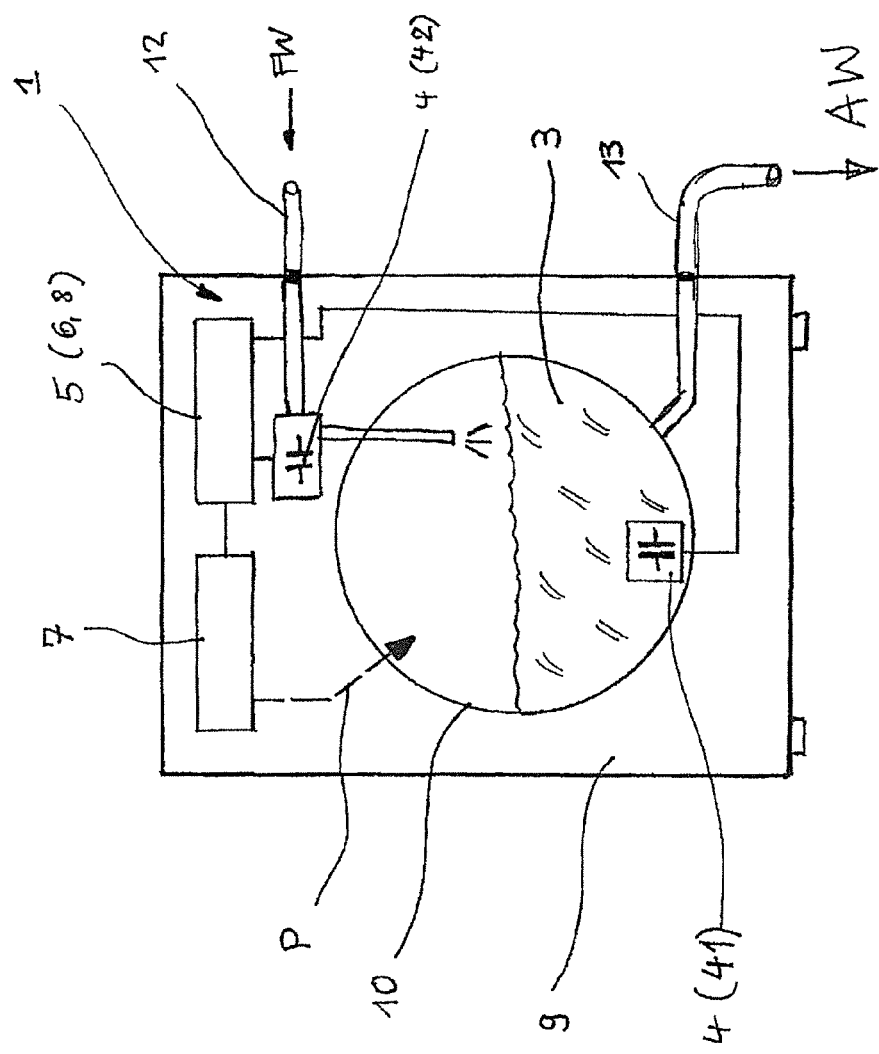
FIG. 2 shows a simplified schematic view of the apparatus according to FIG. 1, disposed, for example, on an appliance.

In FIG. 1, apparatus 1 for detecting the properties of fluid media 3, including sensor unit 4 and control device 5, is shown in general form. FIG. 2, in contrast, shows how the device is arranged inside a washing device 9.

Fluid medium 3 is in a drum 10 or container for the detergent solution in washing device 9, and sensor unit 4 is preferably arranged in a lower region of drum 10 and in communication with control device 5, which comprises actuation device 6 and storage device 8. Control device 5 is connected to the control unit 7 of washing device 9, and an arrow in FIG. 2 indicates, in the same way as in FIG. 1, that the control unit 7 of washing device 9 exerts respective influences on the washing process.

According to FIG. 2, sensor unit 4 is arranged in the bottom part of drum 10, or in the bottom part of a container for the detergent solution (not shown in the Figure), in which container drum 10 is rotatably mounted. An identical or similar sensor unit 4 is also preferably arranged above drum 10 and in communication with a feed pipe 12 for fresh water FW. According to the view shown in FIG. 2, sensor unit 4 thus includes a first sensor 41 in the bottom part of drum 10 and a second sensor 42 in communication with the feed line 12 for fresh water FW. The first sensor 41 of sensor unit 4 is preferably able, therefore, to detect the properties of fresh water shortly after it is fed into washing device 9 and, after the addition of detergent, to detect the detergent solution as the fluid medium 3, whereas the second sensor 42 of sensor unit 4 is preferably arranged in the fresh water feed line and detects the properties of the fresh water FW. This relates in particular to the minerals that are always dissolved in the water, thus allowing the water hardness to be determined.

According to FIG. 2, the present invention thus includes, for example, two sensors 41 and 42 that form sensor unit 4. The invention is not limited to the latter, however. It is also possible, rather, for just one sensor to be provided, for example the first sensor in the bottom part of drum 10, or for more than two sensors to be used. Immediately after the fresh water FW has flowed into the device, and before the washing process begins, the properties and more particularly the water hardness of the fresh water FW (of fluid medium 3) can be determined.

As can be seen from FIG. 2, apparatus 1 may readily be installed in an existing, commercially available washing device 9; consideration need only be given thereby to sensor unit 4 and control device 5. In addition to use in washing appliances, there is also the possibility of applying the inventive arrangement and the associated method to any kind fluid media. In FIG. 2, drum 10 of washing device 9 corresponds to container 2 in FIG. 1. If sensor unit 4 is provided in the form of second sensor 42, container 2 in FIG. 1 corresponds to feed pipe 12 for detecting the properties of fresh water FW fed to the device.

In the same manner, the apparatus according to the invention and the associated method can also be used in a dishwasher or the like, in which a supply of fresh water is needed and other functions of the respective appliance are influenced at least partially by the properties of the fresh water FW and specifically by the water hardness. The present invention is not limited to use in a washing device.

The structure and the manner of operation of apparatus 1 have been described in the foregoing with reference to FIGS. 1 and 2. Details of the inventive method shall now be described with regard to impedance spectroscopy and with reference to a further FIG. 3.

Figure 3:
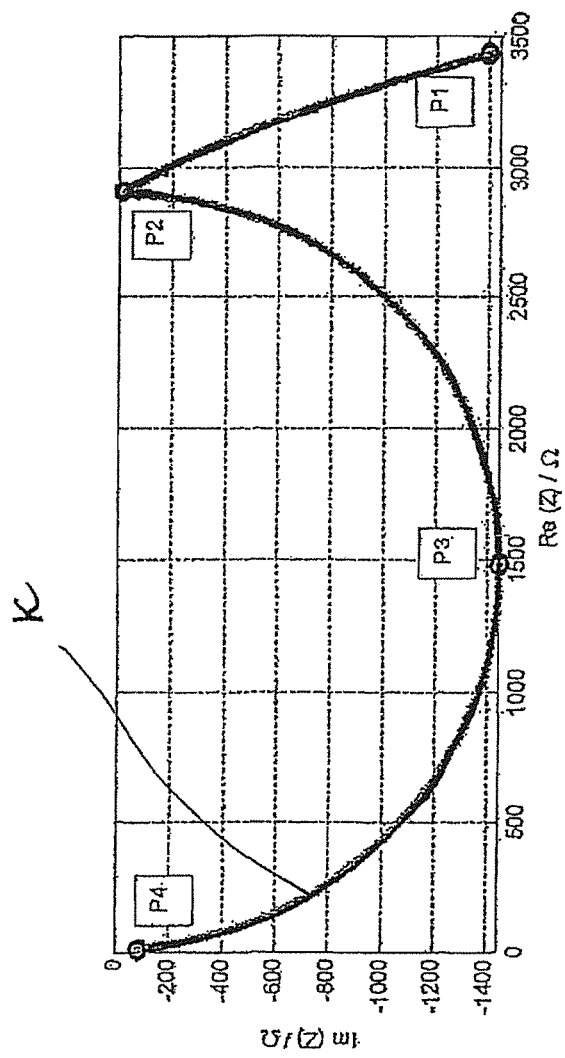
FIG. 3 shows an impedance curve for impedance Z, which plots the imaginary portion against the real portion, and characteristic points P1 to P4.

If at least one of sensors 41 and 42 of sensor unit 4 are actuated by means of control device 5 (actuation device 6) with respective electrical signals to perform a measurement, impedance curves of the real portion and of the imaginary portion of the complex impedance in the impedance plane are obtained for a predetermined frequency range from 1 mHz to 120 MHz, for example. FIG. 3 shows an impedance curve K, in which the x-coordinate shows the real portion of impedance Z and the y-coordinate shows the imaginary portion of impedance Z. The specific properties can be determined from the impedance curve, and from the curve as an individual and characteristic curve for the measurement operation and the fluid medium 3 to be detected. More particularly, properties of fluid medium 3 can be seen from characteristic points P1 to P4 that lie on the detected impedance curve.

The specific data associated with these points, and their position in the impedance spectrum, are dependent on the properties of medium 3 and on the respective frequencies or frequency ranges of the actuation signals. In impedance spectroscopy, detecting the impedance Z with a sensor generally requires that at least two values be detected, as impedance in the context of the physical parameters is a complex variable that can be represented in a complex impedance plane. The real portion Re (Z) and the imaginary portion Im (Z) of the impedance or impedance vector (according to the graph) are determined, from which it is possible to calculate the required values such as the impedance, its amount, its phase angle and the like.

In impedance spectroscopy, the impedance vector is obtained at discrete frequencies over a particular frequency range f (or range of angular velocities ω). More particularly, impedance spectroscopy detects not only the current and voltage, but also the phase angle between these two variables. The test object subjected to impedance spectroscopy is generally the sensor unit 4 (first and second sensor 41 and 42), which allows capacitive and resistive measurement (conductimetry) and which is mainly structured in the form of a parallel-plate capacitor comprising plates 11 (FIG. 1). An electric field is formed between the plates 11 of the parallel-plate capacitor, said field being a unidirectional DC field in the case of DC voltages or an alternating field in the case of AC voltages. A substance to be tested, or in the present case a fluid medium 3 to be tested, such as fresh water or a detergent solution, is located between the plates 11 of the parallel-plate capacitor, so that the special dielectric properties are calculated by performing measurements over a predetermined frequency range. In a broader interpretation, it is also possible on the basis of the calculated dielectric properties to draw conclusions about other properties, such as the concentration of detergent in a detergent solution, or the concentration of foreign matter in fresh water FW.

The simple design of a parallel-plate capacitor as sensor unit 4 (41, 42) serves to illustrate the basic arrangement of a sensor, but other designs are possible and for certain applications are expedient. It is also possible to perform inductive measurements with suitable sensor devices. Capacitive and inductive measurements, as well as conductance measurements can also be performed in combination and in parallel using suitable sensor devices.

In order to actuate sensor unit 4, actuation device 6 of control device 5 may have a test signal generator whose frequency can be set to any desired frequency within a range from 1 mHz to 120 MHz, for example, or 40 Hz to 110 MHz.

As can be seen from the graph in FIG. 3, characteristic points P1 to P4 represent special positions within the detected and measured impedance curve, at discrete frequencies within the predetermined frequency range, according to which the actual signals are formed by actuation device 6. The impedance curve or curve K signifies the end points of a respectively detected impedance vector in the complex impedance plane. FIG. 3 thus shows a graph of the complex function (of the complex impedance) as a Nyquist plot, in which the parameter is frequency.

The present invention shall now be described with reference to the four characteristic points P1 to P4 according to FIG. 3, although the invention is not limited to that number of characteristic points. Fewer or more than four characteristic points may be analyzed. The characteristic points consist of at least two points or a plurality of points that are clearly related to the properties of fluid medium 3. The invention thus relates in general to a predetermined number n of characteristic points P1 to Pn, where n is a natural number. The position of the characteristic points within the complex plane, as shown in FIG. 3, is dependent on the properties of fluid medium 3. Said points are peaks, troughs or transitions along curve K (impedance curve) whose position within the complex plane is characterized by the associated frequency (or angular velocity ω). This frequency is determined by sweeping through part of a predetermined frequency range and by using a mathematical approximation algorithm.

In the following, the method for detecting the properties of fluid medium 3, for example of fresh water FW, shall be described in more detail with regard to water hardness, or with regard to a detergent solution.

Apparatus 1 according to the present invention is structured as shown in FIG. 1, and is disposed, for example, in appliance 9 as shown in FIG. 2. In this context, the properties of fresh water FW, the properties of a detergent solution and the properties of a wastewater, such as wastewater AW to be discharged from washing device 9 by means of a discharge pipe 13. The operation of washing device 9 and the respective operating parameters can be controlled and/or regulated according to the results of detection.

After starting a basic measurement operation in association with impedance spectroscopy, under the control of control device 5, an impedance curve (curve K in FIG. 3) is determined by stipulating a predetermined frequency range Δf or angular velocity range Δω. Sensor unit 4 is actuated with the respective frequency signals in the predetermined frequency range, and the impedance curve (curve K) according to FIG. 3 is obtained in response. The predetermined number of characteristic points (e.g., characteristic points P1 to P4) is determined from the impedance curve obtained by performing measurements across the entire frequency range, and the respective impedance vectors (location points in the complex impedance plane) are determined for said characteristic points Pn (n=4).

The initial impedance curve, as is typical, for example, for the fresh water FW flowing into washing device 9, is determined before the actual commencement of a process, such as a washing process. The measured result, in combination with the initial impedance curve formed by it, is stored in storage device 8, for example, and can be used as a reference value. This curve is referred to in the following as the initial impedance curve.

The fresh water FW (drinking water) supplied by a municipal water utility company is subject to natural and also seasonal variations, so the water hardness may be subject to at least slight changes within tolerance bands gained from experience. If the washing power of washing device 9 is to be improved in respect of efficiency and eco-friendliness, it makes sense to detect even small changes in the hardness of the fresh water FW before the actual washing process begins.

For that purpose, the impedance spectrum of the fresh water FW is measured on an ongoing basis as part of a washing process initiated by the user of washing device 9, and the values obtained are also stored as an initial impedance curve. In the same way as described above with regard to the initial impedance curve, measurement is carried out to obtain an impedance curve as shown in FIG. 3, in which the characteristic points, for example the characteristic points P1 to P4, are determined on the impedance curve (curve K). On the basis of this initial impedance curve and specifically of the characteristic points, for example P1 to P4 in FIG. 3, a water value Xw is detected that can also be referred to as an extended measure of water hardness.

Whereas the hardness of water has been determined until now as the total hardness, which is the concentration of calcium and magnesium ions, detection using impedance to spectroscopy according to the present invention detects other ions that affect the washing process, such as $CU^{2+}$, $Fe^{2+}$, $Fe^{3+}$, $Cl^-$, $SO_4^{2-}$ and $HCO_3^-$ bicarbonate ions. These other components of chemical compounds likewise exert a substantial influence on the washing process or washing program, so these other compounds or components of compounds must be taken into consideration if the washing process is to be controlled or regulated in a very precise manner. In general, the detergents made by producers are adapted to the total hardness and to provide good results, with the dosing of a detergent being done by the user of the washing device according to rough, hitherto known levels of total hardness.

Instead of the normal water hardness, which is also referred to as the total hardness and which is preferably determined by titration in a laboratory, a water value is comprehensively defined according to the present invention as a value $X_w$ which is influenced by the substances or components of substances as described in the foregoing. The water value is thus defined as follows:

$$X_w = f(Ca^{2+}; Mg^{2+}; HCO_3^-; Cu^{2+}, Fe^{2+}, Fe^{3+}, Cl^-, SO_4^{2-}).$$

If this water value is considered as an actual detection value for a comprehensive or extended measure of the total hardness of the fresh water FW, then it is possible to individually dose an amount of detergent, now based on the actual water being used, in order to optimize the washing process. For simple applications, or to provide preliminary information about the properties of the fluid medium 3 in the form of water, a subset of the extended water hardness or water value can be also be used.

In the context of impedance spectroscopy, a regulation concept can be designed that takes into consideration the extended measure of water hardness (the water value) and the dirtiness of the laundry, in order to determine, for example, a reasonable amount of a detergent and duration of a washing program (process), thus achieving efficacious cleaning of the laundry, while simultaneously ensuring that the environmental impact of the washing process is minimized.

In addition to detection of the current comprehensive water hardness, which according to the above description can be referred to as the water value, it is possible to detect the detergent solution of the washing device, or the water in the separate rinsing operations after the washing process has been completed, in the same way once again using impedance spectroscopy and for an identical frequency range and hence with identical actuation of sensor unit 4 by means of control device 5. The efficacy of individual washing processes can thus be determined relative to the water value determined at the outset, taking into account a number of factors affecting the washing process. The water value Xwo determined at the outset is based on the initial impedance curve that was detected.

The impedance spectrum of wastewater AW is thus detected by means of impedance spectroscopy for further rinsing operations when rinsing the laundry in washing device 9, with an impedance curve K according to FIG. 3 preferably being detected and formed in the same manner in the equivalent frequency range of the actuation signals for sensor unit 4. The respective characteristic points are likewise formed in a similar frequency range. The various detections carried out during the required rinsing operations are referred to as current measurements.

If it is intended to curtail the amount of data processing involved and to increase the measurement activity (detections) within a unit of time, the frequency ranges around the respective characteristic points P1 to P4 of the previously measured initial impedance curve for the water value are defined as surrounding frequency ranges, in which the measurement is carried out. The surrounding frequency ranges are defined with approximate knowledge of the fluid medium 3 to be tested, and in respect of their position and in their scope in the complex impedance plane. A limitation is imposed in this way on the detection of the current properties of fluid medium 3, for example of the detergent solution during the washing process or of the wastewater AW to be discharged after rinsing operations, namely a limitation to the surrounding frequency ranges of the respective characteristic points, such as points P1 to P4 according to FIG. 3. This means there is no need to detect the entire impedance curve again, as shown in FIG. 3, for example. Instead, the respective characteristic points (at least one, or several, or all of points P1 to P4) of a new current impedance curve (i.e., of a current measurement or detection) are determined within the previously determined surrounding frequency ranges, so that only some parts of the impedance curve in the region of the surrounding frequency ranges need to be processed.

As regards the dependence of the position of the characteristic points on the kind of fluid medium 3, or on the properties thereof, as stated above, there is also a relationship between the associated surrounding frequency ranges and fluid medium 3. For that reason, the surrounding frequency ranges are preferably determined as a region around the respective characteristic points (e.g., P1 to P4), preferably with knowledge of the kind of fluid medium being detected, and taking into consideration the process to be carried to out (such as a washing process, for example) and hence the detection results that can likely be expected (current impedance curves).

With every rinsing operation carried out in a washing device, more and more residues of dissolved dirt and used detergent are rinsed out of the laundry and discharged, with the result that the respective wastewater AW from each rinse is separately tested according to the present invention by means of a current detection. If this test produces a respective difference, in the respective surrounding frequency ranges of the characteristic points of the initial impedance curve calculated at the beginning of the washing process, from the currently measured characteristic points within these surrounding frequency ranges, then said difference is a measure for the change in the properties of the water being used, from the fresh water FW initially supplied to the wastewater AW to be discharged after a rinsing operation. More specifically, a difference ensues here between the characteristic point as initially calculated, P2 for example, and the corresponding characteristic point P2 measured in the same surrounding frequency range in the subsequent measurements of the wastewater, thus leading to changed properties of the water and thus to a different position of point P2 in the complex impedance plane (FIG. 3), due to the at least slight contamination of the dirty water or wastewater AW resulting from the rinsing operation. This applies for all the determined characteristic points, for example points P1 to P4 in FIG. 3, although the present invention is not limited in the number of these points. The step of determining the difference between the characteristic points P1 to P4 thus involves determining the difference between respective corresponding characteristic points P1 to P4 within the respective surrounding frequency range.

Figure 4:
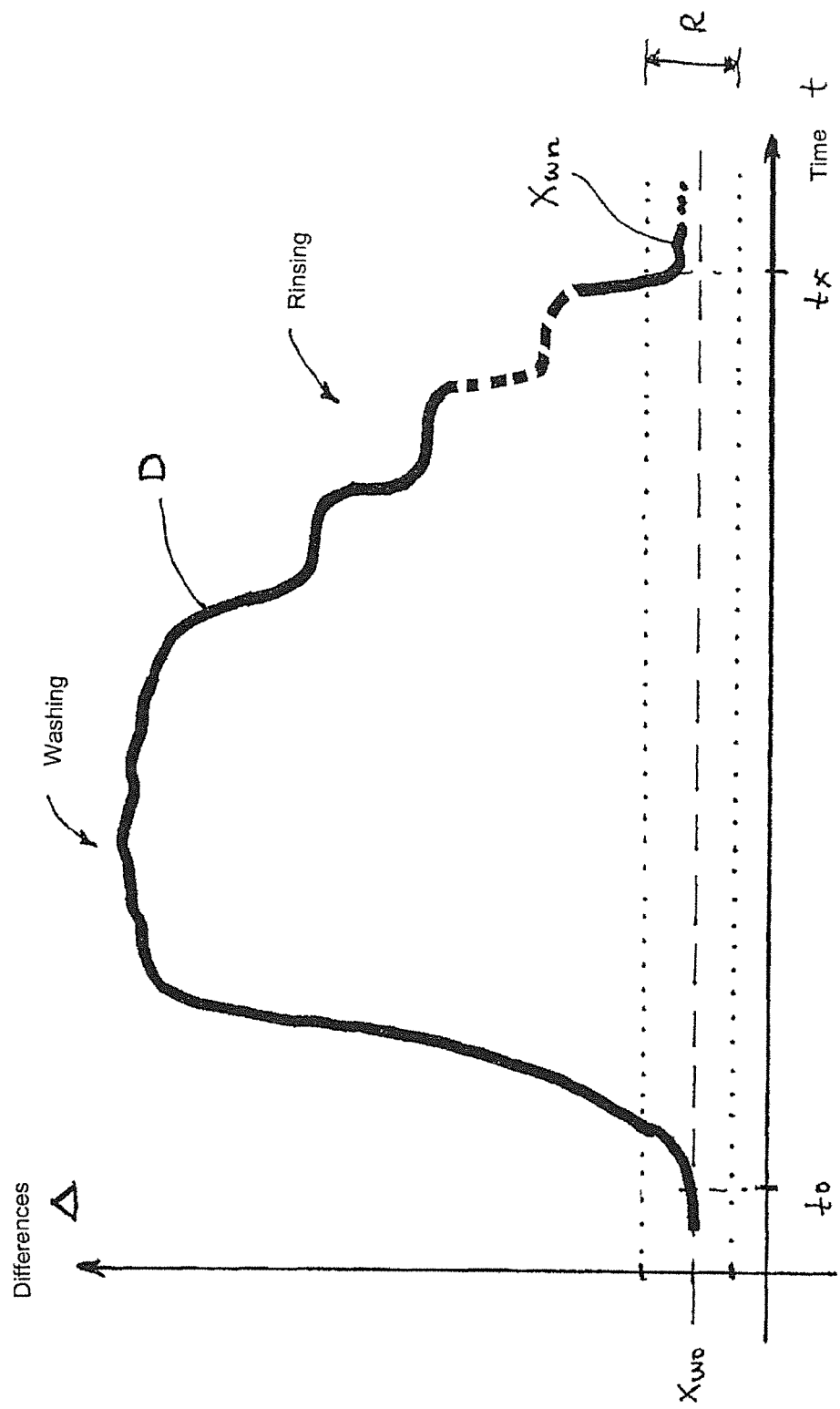
FIG. 4 shows a graph illustrating differences obtained by comparing corresponding characteristic points of different detections.

For each of the characteristic points, the differences from the initially performed measurement (initial impedance curve) are calculated using current detections, and at least one difference range is defined as reference range R according to FIG. 4, with which the respective, actually measured differences (gaps) associated with the respectively measured characteristic points P1 to P4 are compared. In this connection, FIG. 4 shows a curve D representing a series of calculated differences associated with current detections, relative to the initial impedance curve and associated with the current detections in surrounding frequency ranges of the characteristic points of the initial impedance curve. Determining the difference between the characteristic points thus includes the step of determining the difference between respective corresponding characteristic points P1 to P4 within the respective surrounding frequency range.

The curve or difference curve D therefore illustrates increasing and decreasing dirtiness of the initially detected fresh water (water value) in the course of the process being described here for the example of a washing process (and corresponding to continuously changing properties of fluid medium 3). In FIG. 4, the horizontal axis represents time and the vertical axis represents the differences Δ between the characteristic points measured at the beginning of the washing process and the characteristic points measured in the course of the washing process within the frequency range surrounding the initially measured characteristic points.

If the calculated difference that is obtained as a result of this comparison is outside reference range R (which may lie within the surrounding frequency range of the initially measured characteristic points P1 to P4 of the complex impedance plane), it is concluded from that fact that the wastewater AW to be discharged after a rinsing operation is still relatively contaminated, and hence that it is necessary to perform another rinsing operation in the predetermined or previously programmed manner. If, in contrast, the difference for one of characteristic points P1 to P4 is within reference range R, it is determined that the contamination of the water relative to the initially supplied fresh water has reached a reasonable minimum, and hence that another rinsing operation can be dispensed with. In such a case, control device 5 can instruct control unit 7 of washing device 9 not to perform any further rinsing operations and to stop the washing process after a respective spin drying step.

In combination with the respective measurements of wastewater AW from individual rinsing operations, and by determining the continuously changing properties of the water in the course of the process by means of impedance spectroscopy, it is therefore determined whether a degree of contamination is within a predetermined range that is permitted or desired (i.e., reference range R within the surrounding frequency range). Depending on the result of comparison, specific measures can thus be taken to control and/or regulate washing device 9 (of the process). The detection results obtained from initial detection and preferably from all other detections within the process are stored in storage device 8 for further processing and analysis.

In this manner, it is possible to control or to regulate the washing processes of washing device 9 such that the laundry is optimally cleaned and thoroughly rinsed, while also minimizing the environmental impact. By means of the arrangement according to the invention and the associated method, the sensor system and the evaluation devices, for example in the form of control device 5, can be arranged in a customary washing device such that a modern and commercially available washing device can be equipped or retrofitted with such sensors in a simple and inexpensive manner. By means of the inventive arrangement, it is thus possible to obtain precise measurements without an elaborate laboratory being required, and without additives that are needed in the laboratory, such as reagents, being required. For a user, the properties of the fluid medium, for example of fresh water FW and of wastewater AW relative to fresh water FW, can be detected and analyzed automatically and without manual intervention.

The reference range R in FIG. 4 was described in the foregoing as a single region which can be applied for all the characteristic points that are used, such as characteristic points P1 to P4 in FIG. 3, for example. Every individual difference is evaluated relative to said reference range R. Alternatively, an individual reference range can be determined for each of the characteristic points P1 to P4, for example an associated reference range R1 to R4, whereby it is necessary to define as a basic condition when the permissible minimum level of contamination has been reached, if one part of the characteristic points detected when measuring the wastewater is within the respective reference range and another part of the characteristic points is outside the respective reference range. The reference range R for the differences between the respective characteristic points has an upper and a lower limit. The upper and lower limits are defined according to respective predetermined differences from the initial value Xwo. The upper and the lower limits of the range of differences may also be determined according to the kind of process.

FIG. 4 thus shows the curve D of detected values for the initially supplied fresh water and for the quality of wastewater in the individual rinsing operations, and also, where relevant, for the properties of the detergent solution; before the washing program as a whole is stopped, it is calculated whether the altered properties of the wastewater in comparison to those of the fresh water are within a predetermined region R.

The difference curve D according to FIG. 4 represents the respectively detected differences between the impedance curves, and in particular between the respective characteristic points P1 to P4, as obtained from the entire set of measurements from the commencement of fresh water supply to the last discharge of rinsing water. At time t0, fresh water FW flows into washing device 9, at which point a water value is determined, in association with the initial impedance curve, as initial water value Xwo. Reference region R lies symmetrically or asymmetrically around initial water value Xwo.

At later times, detergent is added and the process is continued in the form of the washing process. At yet later times, the laundry is rinsed several times, the properties of fluid medium 3 being determined continuously or cyclically at short intervals, as are the properties of the detergent solution or the rinsing water in the case under consideration here. The contamination of the water to be discharged becomes less with each rinsing operation, so the difference curve D approaches the initial water value Xwo due to decreasing differences. If the differences associated with the characteristic points (for example, P1 to P4), according to the currently detected impedance curve, are within reference range R on the n-th rinsing operation, which occurs at time tx in the graph shown in FIG. 4, the washing process (the process) can be stopped after that time with the usual measures included in the washing program.

In the overall program which controls the process, for example the washing process, and which is stored and processed in control unit 7, it is possible for rinsing operations, for example, to be stored as a standard operation. The rinsing operation is carried out with a predefined duration and with a predetermined amount of water. In combination with the detection results obtained from impedance spectroscopy, it is possible to control or regulate the rinsing operations by intervening accordingly. Depending on the measurement result, the latter operations may be performed for a shorter or longer duration, and/or the amount of water may be altered. With dynamic detection, i.e. with cyclic detection of the fluid medium 3 (fresh water, detergent solution, rinsing water), the rinsing parameters (duration and amount of water) can be varied in order to control or regulate rinsing.

Thus, in combination with the continuous or cyclic measurement of the water value or water properties, including the properties of a detergent solution using impedance spectroscopy, a difference curve D is obtained as a plot over time of differences relative to the initially determined water value Xwo, depending on which it is possible, in combination with predetermined threshold values and a predetermined reference range R, to influence the control and/or the regulation of washing device 9 and hence to influence the control and/or the regulation of the washing process that is currently being performed.

With the difference curve D which is shown in FIG. 4 and which relates to the continuously or cyclically measured water value Xw, it is possible to conduct an analysis or evaluation of differential impedance curves, with measurements or detections only being carried out in a predetermined region of the entire impedance curve, for example in the surrounding frequency ranges of characteristic points P1 to P4, and with gaps or differences being determined in the analysis that form a measure for the changing properties, for example of the water in the washing device in the course of a washing process. By analyzing the differential impedance curves, it is possible to perform the washing process individually for a particular amount of laundry, for a particular amount of detergent and for particular basic properties of the fresh water that is supplied, such that good results of washing and an ecofriendly washing process are ensured. By defining the reference range, which is determined with regard to environmental aspects in terms of the contamination level of the water, it is possible to avoid the number of rinsing operations being unnecessarily large, so that the amount of fresh water that is consumed is limited to the necessary amount, while still ensuring at the same time that the washed laundry contains hardly any residues of dirt or detergent.

According to the method and associated apparatus (FIGS. 1 and 2) described in the foregoing, apparatus 1 thus includes all the devices required to carry out the method. Control device 5, actuation device 6 and sensor device 4 form a device (4, 5, 6) for detecting an initial impedance curve, including a plurality of characteristic points (P1 to P4) on said initial impedance curve K on the complex impedance plane and determining an initial value Xwo of the properties of fluid medium 3. Control device 5 and storage device 8 form a device (5, 8) for determining respective surrounding frequency ranges around each of the characteristic points according to the initial impedance curve and conducting further detection of current impedance curves within the respective surrounding frequency ranges around the characteristic points of the initial impedance curve, determining respective characteristic points of the current detections within the surrounding frequency ranges of the initial impedance curve K. Control device 5 and storage device 8 form a device (5, 8) for determining respective characteristic points of the current detections within the surrounding frequency ranges of the initial impedance curve, and for determining respective characteristic points of the current detections within the surrounding frequency ranges of the initial impedance curve, and control device 5 and storage device 8 form a device (5, 8) for determining differences between the characteristic points of each of the current detections of the impedance curve for at least one of the characteristic points and the respective corresponding characteristic point on the initial impedance curve, and comparing the difference with a predetermined reference range R, and conducting control measures on the process for the purpose of continuing said process if the difference is within the reference range (R).

A second embodiment of the present invention shall now be described.

According to the second embodiment of the present invention, the same apparatus 1 is provided as described with reference to the first embodiment in FIGS. 1 and 2.

In the second embodiment, apparatus 1 and specifically control device 5 includes the possibility of performing measurements or detections by means of cyclic voltammetry (CV), in addition to the devices and possibilities of the first embodiment and hence in addition to the option of performing any number of detections by means of impedance spectroscopy (detection of impedance curves). The method of cyclic voltammetry (referred to hereinafter as "voltammetry") can be performed independently of impedance spectroscopy, and control device 5 and specifically actuation device 6 can use the same sensor unit 4 with first sensor 41 and second sensor 42 to perform detection by voltammetry. Measurements in connection with impedance spectroscopy and measurements in connection with voltammetry are performed successively or intermittently using the same sensor. At any given moment, a respective sensor is actuated by actuation device 6 only in connection with one of the detection methods.

More specifically, voltammetry uses a triangular voltage for actuating the sensor unit(s), with the response in current being detected via the sensor unit 4 (41 or 42) that is in contact with the fluid medium 3. The triangular voltage is in the mHz range and pertains to only one single frequency or to a few individual frequencies. In contrast to voltammetry, the impedance spectroscopy method generally uses voltage with a sinusoidal waveform in the range from about 0.1 Hz to 110 MHz, with detections being made for a very large number of single frequencies.

The detection results obtained with impedance spectroscopy are plotted as a function of frequency, whereas the detection results obtained with voltammetry are plotted as a function of time.

Figure 5:
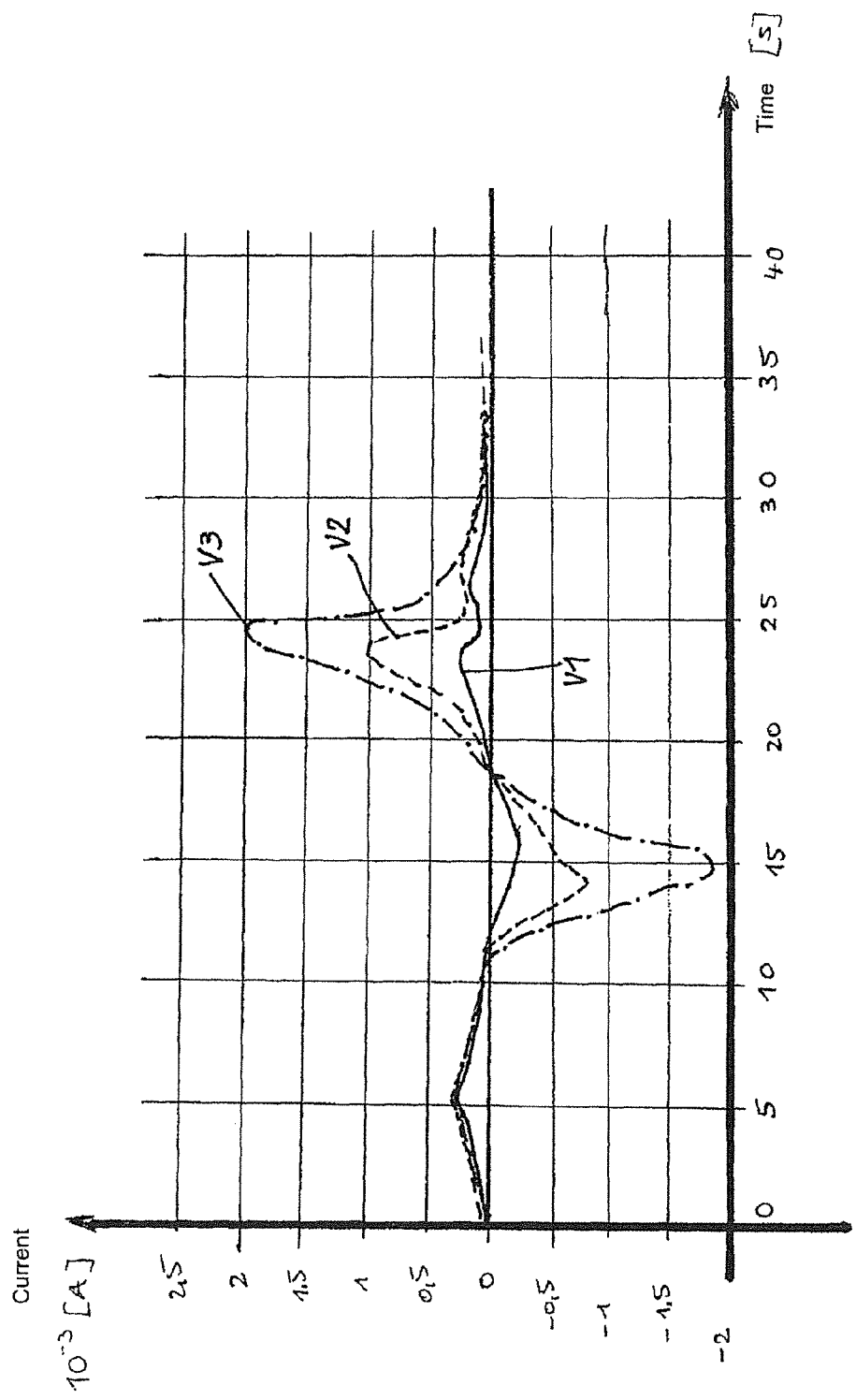
FIG. 5 shows a graph illustrating an application of voltammetry.

FIG. 5 shows a detection result obtained using cyclic voltammetry, in which the detected response in current is dependent on the total hardness for a respective predefined voltage (triangular voltage). Curve V1 (the solid line) shows a measurement result for water with a hardness of 2.8° dH ("German hardness" scale). Curve V2 (the broken line) is obtained from measuring water having a hardness of 8.4° dH, and curve V3 (the dot-dash line) shows a detection result for water having a hardness of 14° dH. FIG. 5 shows the respective curves (response in current) plotted as a function of time over a period of several seconds. The horizontal axis indicates the time, and the vertical axis indicates the detected current.

The methods of impedance spectroscopy and voltammetry may be applied independently of each other in order to determine the properties of fluid medium 3, for example water having different properties. More particularly, voltammetry may be used to supplement impedance spectroscopy.

Detection using the method of impedance spectroscopy was described above with reference to the first embodiment, in which the measurements were carried out in the surroundings of the previously determined characteristic points (P1 to P4, for example). According to the second embodiment, measurements can be carried out additionally using the voltammetry method, and the curves and data thus obtained can be stored (FIG. 5). The properties of fluid medium 3, for example the properties of the water and specifically the water value, are calculated from the detection results obtained with impedance spectroscopy and voltammetry, and those detection results represent respective initial curves in the same way as in the first embodiment. On this basis, and in connection with a washing process as an example, a basic amount of detergent can be determined from the water data calculated from the detection results obtained using impedance spectroscopy and voltammetry. This corresponds to time t0 in FIG. 4, at which the initial impedance curve and also the initial voltammetry curve are formed, and which are used as a starting point for the subsequent process.

In said process, taking the example of the washing process, a basic amount of detergent is added and the washing process begins. This can be seen clearly in FIG. 4, in that the properties of the fluid medium 3 now present in the form of a detergent solution have changed substantially relative to the initial values (water value Xwo) (large differences). As in the first embodiment, detection can be carried out continuously or cyclically using impedance spectroscopy, with the detected curves and data being stored accordingly. This is again linked to determination of the characteristic points (position of the characteristic points and the surrounding frequency ranges). If need be, further measurements may be taken using impedance spectroscopy, with the respective characteristic points being monitored and compared with the initial detection results or also with current interim results. It is possible in this manner to track the properties of the detergent solution (FIG. 4). With regard to appropriate control or regulatory measures, it is possible on the basis of the detection results and the comparisons made (difference curve in FIG. 4) to calculate any shortage of detergent and to add detergent accordingly.

If the main washing process within the overall program has been completed and rinsing operations are initiated, then the measurements are likewise taken by means of impedance spectroscopy and current detection results are compared, for example, with the initial impedance curve (initial fresh water value Xwo), until the current detection result shows differences (deviations) as indicated in FIG. 4 and which ultimately lie within reference range R.

Parallel to the plurality of rinsing operations, the detection results obtained by voltammetry are likewise recorded and compared with initially detected data (initial voltammetry curves). When the detection results from impedance spectroscopy and from voltammetry are taken into account (i.e., when the results are correlated), it is possible to determine very precisely when the individual rinsing operations may be stopped, because the detection results for the properties of the water are within reference range R. The respective detection results obtained using impedance spectroscopy and voltammetry can be correlated with each other in this connection and compared with each other, for example.

By using impedance spectroscopy and by using voltammetry in addition, the same advantages can be achieved as those described in connection with the first embodiment.

The invention and its manner of operation were described in the foregoing with reference to a washing process in a washing device (washing machine). However, the present invention is not limited in application to washing devices of the kind described. Other, similar processes may be influenced, for example dishwashers may also be equipped with the invention so that the rinsing operations of a dishwasher can be controlled in an identical manner. It is also possible to check the properties of water continuously or also cyclically in various areas within private households, in industry or also in nature, in order to identify desired and undesired deviations from predetermined base values. For example, when rainwater is stored it is possible to calculate when, in the event of rain, the collected water has a minimum level of contamination (due to contamination of the air, for example, or of the collection area). If the minimum permissible contamination has been reached, the checked water can be fed to a collecting tank.

By means of the simple arrangement that does not involve any manual intervention, and with the possibility of digital storage and further processing of the information obtained, the devices and the associated methods can be applied in many areas of private households, in industry and in nature. There are also many potential applications in municipal waterworks companies.

The invention has been described in the foregoing with reference to embodiments. However, it is self-evident for a person skilled in the art that the configuration of the present invention according to the Figures described in the foregoing, and the parts and components shown in the Figures and the description, as well as the further details provided by way of example, are not to be interpreted in a restrictive sense. The invention is not limited to the views shown in the Figures, or, more specifically, to specific dimensions and arrangements. All embodiments and variants which come under the enclosed claims are considered as belonging to the invention.

What is claimed is:

1. A method of detecting properties of fluid media within a washing process of a washing device, using impedance spectroscopy, said method comprising the steps of:
    a) before commencement of said washing process, detecting an initial impedance curve over a frequency range of a test signal generator associated with said impedance spectroscopy, including a plurality of characteristic points on said initial impedance curve in a complex impedance plane, and determining an initial value for the properties of the fluid medium,
    b) determining respective surrounding frequency ranges around each of the characteristic points according to the initial impedance curve,
    c) conducting further detections of current impedance curves within the respective surrounding frequency ranges around the characteristic points of the initial impedance curve,
    d) determining respective characteristic points for the currently detected impedance curve within the surrounding frequency ranges of the initial impedance curve,
    e) determining differences between the characteristic points for each of the current detections of the impedance curve for at least one of the characteristic points and the respective corresponding characteristic point on the initial impedance curve, and comparing the difference with a predetermined reference range, and
    f) performing control measures on the washing process and continuing said washing process of the washing device if the difference is within the predetermined reference range.

2. The method according to claim 1, wherein the reference range is determined according to the initial value of the properties of the fluid medium, and the initial value of the properties is within the reference range.

3. The method according to claim 2, wherein the step of determining the difference between the characteristic points includes the step of determining the difference between respective corresponding characteristic points within the respective surrounding frequency range.

4. The method according to claim 3, wherein the step of determining the difference between the respective characteristic points includes the step of determining the difference individually for each of the characteristic points or for all the characteristic points used.

5. The method according to claim 2, wherein the washing process is of a certain kind, wherein the reference range for differences between respective characteristic points has an upper and a lower limit, and the upper and lower limits are defined according to respective predetermined differences from the initial value and wherein the upper and the lower limits of said reference range is determined according to the kind of said washing process.

6. The method according to claim 5, wherein the method includes the step of detecting the properties of the fluid medium by means of voltammetry, and correlating the detection results using voltammetry with the detection results using impedance spectroscopy in order to form a total result for the properties of the fluid medium.

7. The method according to claim 1, wherein the step of determining the difference between the characteristic points includes the step of determining the difference between respective corresponding characteristic points within the respective surrounding frequency range.

8. The method according to claim 7, wherein the step of determining the difference between the respective characteristic points includes the step of determining the difference individually for each of the characteristic points or for all the characteristic points used.

9. The method according to claim 1, wherein the predefined process is of a certain kind, wherein the reference range for differences between respective characteristic points has an upper and a lower limit, and the upper and lower limits are defined according to respective predetermined differences from the initial value and wherein the upper and the lower limits of said reference range is determined according to the kind of said predefined process.

10. The method according to claim 1, wherein the method includes the step of detecting the properties of the fluid medium by means of voltammetry, and correlating the detection results using voltammetry with the detection results using impedance spectroscopy in order to form a total result for the properties of the fluid medium.

11. The method according to claim 1, wherein the fluid media is water in the washing device and the washing process is a control of the washing device.

12. An apparatus for performing the method of detecting properties of fluid media using impedance spectroscopy within a washing process of a washing device, said apparatus comprising:
a) a device for detecting an initial impedance curve over a frequency range of a test signal generator associated with said impedance spectroscopy before commencement of said washing process, said detecting of the initial impedance curve including a plurality of characteristic points on said initial impedance curve in a complex impedance plane, and determining an initial value of the properties of the fluid medium,
b) a device for determining respective surrounding frequency ranges around each of the characteristic points according to the initial impedance curve, and for conducting further detections of current impedance curves within the respective surrounding frequency ranges around the characteristic points of the initial impedance curve,
c) a device for determining respective corresponding characteristic points of the current detections within the surrounding frequency ranges of the initial impedance curve, and determining respective corresponding characteristic points for the currently detected impedance curve within the surrounding frequency ranges of the initial impedance curve, and
d) a device for determining differences between the characteristic points of each of the current detections of the impedance curve for at least one of the characteristic points and the respective corresponding characteristic point on the initial impedance curve, and for comparing the difference with a predetermined reference range, and for performing control measures on the washing process and continuing said washing process of the washing device if the difference is within the predetermined reference range.

13. An apparatus according to claim 12, wherein the control device is provided to determine the characteristic points at predetermined frequencies within the surrounding frequency range.

14. The apparatus according to claim 13, wherein the device has a sensor device for conducting detections in respect of the fluid medium, and the control device is provided to actuate the sensor device to conduct detections using impedance spectroscopy or voltammetry.

15. The apparatus according to claim 12, wherein the device has a sensor device for conducting detections in respect of the fluid medium, and the control device is provided to actuate the sensor device to conduct detections using impedance spectroscopy or voltammetry.

16. The method according to claim 12, wherein the fluid media is water in a the washing device and the washing process is a control of the washing device.

* * * * *